(12) United States Patent
Chowhan et al.

(10) Patent No.: US 8,921,337 B2
(45) Date of Patent: Dec. 30, 2014

(54) CARBOXYVINYL POLYMER-CONTAINING NANOPARTICLE SUSPENSIONS

(75) Inventors: Masood A. Chowhan, Arlington, TX (US); Malay Ghosh, Fort Worth, TX (US); Bahram Asgharian, Arlington, TX (US); Wesley Wehsin Han, Arlington, TX (US)

(73) Assignee: Alcon Research, Ltd., Fort Worth, TX (US)

( * ) Notice: Subject to any disclaimer, the term of this patent is extended or adjusted under 35 U.S.C. 154(b) by 486 days.

(21) Appl. No.: 12/957,864

(22) Filed: Dec. 1, 2010

(65) Prior Publication Data

US 2011/0135743 A1    Jun. 9, 2011

Related U.S. Application Data

(60) Provisional application No. 61/266,368, filed on Dec. 3, 2009.

(51) Int. Cl.
*A61K 31/765* (2006.01)
*A61K 9/00* (2006.01)
*A61K 47/02* (2006.01)
*A61K 9/10* (2006.01)
*A61K 31/165* (2006.01)
*A61K 47/32* (2006.01)
*A61K 47/36* (2006.01)
*A61K 9/14* (2006.01)

(52) U.S. Cl.
CPC .............. *A61K 9/0048* (2013.01); *A61K 47/02* (2013.01); *A61K 9/146* (2013.01); *A61K 9/10* (2013.01); *A61K 31/165* (2013.01); *A61K 47/32* (2013.01); *A61K 47/36* (2013.01)
USPC ............................ 514/54; 514/59; 424/78.04

(58) Field of Classification Search
USPC .................................. 514/54, 59; 424/78.04
See application file for complete search history.

(56) References Cited

U.S. PATENT DOCUMENTS

| | | | |
|---|---|---|---|
| 4,313,949 A | 2/1982 | Shanklin, Jr. et al. | |
| 5,188,826 A | 2/1993 | Chandrasekaran et al. | |
| 5,192,535 A | 3/1993 | Davis et al. | |
| 5,461,081 A | 10/1995 | Ali et al. | |
| 5,475,034 A | 12/1995 | Yanni et al. | |
| 6,403,609 B1 | 6/2002 | Asgharian | |
| 6,486,138 B1 | 11/2002 | Asgharian et al. | |
| 6,583,124 B2 | 6/2003 | Asgharian | |
| 6,838,449 B2 | 1/2005 | Asgharian | |
| 7,169,767 B2 | 1/2007 | Asgharian | |
| 2002/0183280 A1* | 12/2002 | Asgharian | 514/54 |
| 2003/0232089 A1 | 12/2003 | Singh et al. | |
| 2006/0257486 A1 | 11/2006 | Owen et al. | |
| 2006/0257487 A1 | 11/2006 | Owen et al. | |
| 2009/0270345 A1 | 10/2009 | Ketelson et al. | |
| 2010/0196415 A1 | 8/2010 | Davis et al. | |

FOREIGN PATENT DOCUMENTS

JP  2007-119456  5/2007

OTHER PUBLICATIONS

Kassem, et al,"Nanosuspension as an ophthalmic delivery system for certain glucocorticoid drugs", Intl Journal of Pharmaceutics, vol. 340:126-133, 2007.

* cited by examiner

*Primary Examiner* — Zohreh Fay
(74) *Attorney, Agent, or Firm* — Mark E. Flanigan

(57) ABSTRACT

The present invention generally relates to suspension compositions having a carboxyvinyl polymer such as a carbomer, a galactomannan such as guar, and a borate compound. A sparingly soluble particulate compound such as nepafenac is also included in the compositions. The sparingly soluble particulate compound has a small particle size to enhance bioavailability of the compound.

15 Claims, 3 Drawing Sheets

CARBOXYVINYL POLYMER-CONTAINING NANOPARTICLE SUSPENSIONS

CROSS-REFERENCE TO RELATED APPLICATION

This application claims priority under 35 U.S.C. §119 to U.S. Provisional Patent Application Ser. No. 61/266,368, filed Dec. 3, 2009, the entire contents of which are incorporated herein by reference.

TECHNICAL FIELD OF THE INVENTION

The present invention relates to compositions for ophthalmic drug delivery, and more specifically to nanoparticle suspensions comprising a carboxyvinyl polymer, a galactomannan, and borate.

BACKGROUND OF THE INVENTION

The topical administration of pharmaceuticals for ophthalmic indications is generally preferred for ease of use and patient compliance. Aqueous solutions having physiologically-compatible pH and osmolality are representative of delivery systems in this class. However, many pharmaceutical agents are relatively insoluble in aqueous vehicle and must be delivered as a suspension. Often, such agents do not penetrate corneal tissue well. Suspensions can be diluted or flushed from the eye by the tear film before the agent is able to enter the corneal tissue in sufficient concentration.

Accordingly, various techniques have been used to improve the overall bioavailability of sparingly soluble pharmaceutical agents and increase the concentration of such agents in targeted tissues. Increasing the viscosity of topically applied solutions to increase the retention time of the solution on the cornea does not always lead to an increase in bioavailability, and may actually retard penetration of the pharmaceutical agent into the cornea. See, e.g., U.S. patent application Ser. No. 11/429,736, filed May 8, 2006 and entitled "Suspension Formulations of Nepafenac and other Ophthalmic Drugs for the Topical Treatment of Ophthalmic Disorders".

Ophthalmic compositions have been previously described that utilize galactomannan-borate gelling systems. U.S. Pat. No. 6,403,609 to Asgharian, entitled "Ophthalmic compositions containing galactomannan polymers and borate," describes such systems and is herein incorporated by reference in its entirety.

Ophthalmic compositions that enhance the corneal penetration of sparingly soluble pharmaceutical agents such as nepafenac have been disclosed in U.S. patent application Ser. No. 11/430,239 filed May 8, 2006 entitled "Suspension Formulations of Nepafenac and other Ophthalmic Drugs for Topical Treatment of Ophthalmic Disorders". The '239 application describes the use of poloxamer or meroxapol surfactant and a glycol tonicity-adjusting agent in compositions having good corneal permeability of the active pharmaceutical. These compositions do not comprise a carboxyvinyl polymer.

U.S. Pat. No. 5,188,826 discloses an ophthalmic gel suspension for treating dry eye. The suspension compositions remain as a gel in the eye for a prolonged time, and release water and one or more ophthalmic demulcents or vasoconstrictors. The suspension compositions contain a water-insoluble, lightly cross-linked, carboxyl containing polymer having a particle size of not more than 50 μm in equivalent spherical diameter. The demulcent is preferably at least one of sodium carboxymethyl cellulose, hydroxyethyl cellulose, hydroxypropylmethyl cellulose, methyl cellulose, dextran 70, gelatin, glycerin, polyethylene glycol, polysorbate 80, propylene glycol, polyvinyl alcohol or polyvinylpyrrolidone. Particularly preferred as the carboxyl-containing polymer is CARBOPOL® 976. The suspension compositions do not contain a prescription drug.

U.S. Pat. No. 5,192,535 discloses suspension compositions of ophthalmic drugs that have suitably low viscosities to permit easy administration in drop form, but which rapidly gel in the eye to provide sustained drug release. The suspension compositions are formulated at a pH of from about 3 to about 6.5 and contain a water-insoluble, carboxyl-containing polymer prepared by polymerizing one or more carboxyl-containing monoethylenically unsaturated monomers and less than about 5% by weight of a cross-linking agent. CARBOPOL® 976 and polycarbophil are identified as examples of suitable carboxyl-containing polymers. These formulations gel in the eye due to the thermogelling properties of the polymers. Ion exchange resins may be included as one type of adjuvant in the suspension compositions. Demulcents are identified as one of many types of medicaments suitable for use in the suspension compositions.

BRIEF SUMMARY OF THE INVENTION

The present invention generally relates to topical aqueous ophthalmic nanoparticle suspensions comprising a sparingly soluble particulate compound (e.g., pharmaceutical agents), carboxyvinyl polymer, galactomannan, and borate. A preferred composition of the present invention is a nepafenac suspension comprising a carboxyvinyl polymer of acrylic acid cross-linked with allyl sucrose or allylpentaerythritol, guar, and boric acid.

Compositions of the present invention are physiologically compatible and provide good bioavailability for sparingly soluble particulate compounds such as nepafenac, even at infrequent dosing intervals such as once or twice daily. Maintaining the viscosity of carboxyvinyl polymer solutions is generally quite difficult, as the viscosity imparted by carboxyvinyl polymer is very sensitive to salt concentration; accordingly such solutions often do not comprise sodium chloride. However, as the tear film comprises a relatively high concentration of sodium chloride, the viscosity of a carboxyvinyl polymer solution typically decreases once topically applied to the eye. The present inventors have found that the viscosity of carboxyvinyl polymer solutions can be maintained if the solution also contains a galactomannan and borate. The carboxyvinyl polymer, galactomannan, and borate compositions of the present invention have a stable viscosity when applied to the eye, and provide for good bioavailability of sparingly soluble particulate compounds. The present inventors have also found that a reduced particle size of 50 to 700 nm improves the bioavailability of such compounds in target tissues using topical ophthalmic suspensions.

The foregoing brief summary broadly describes the features and technical advantages of certain embodiments of the present invention. Additional features and technical advantages will be described in the detailed description of the invention that follows.

BRIEF DESCRIPTION OF THE DRAWINGS

A more complete understanding of the present invention and the advantages thereof may be acquired by referring to the following description, taken in conjunction with the figures of the accompanying drawing in which like reference numbers indicate like features and wherein.

DETAILED DESCRIPTION OF THE INVENTION

Figure 1:
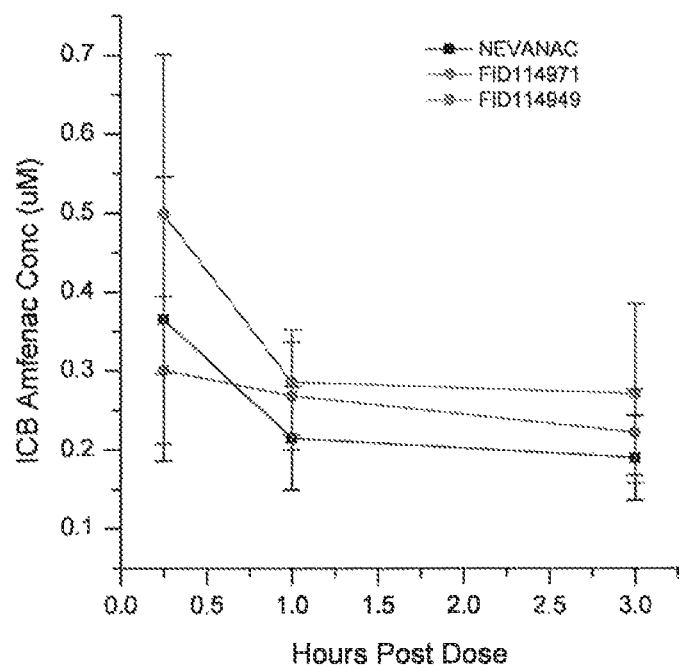
FIG. 1 is a graph showing the concentration of amfenac (a nepafenac metabolite) in the rabbit iris ciliary body following administration of topical nepafenac formulations.

Compositions of the present invention comprise a carboxyvinyl polymer. The carboxyvinyl polymers have an approximate molecular weight of from about 50,000 to about 6 million daltons. The polymers are characterized as having carboxylic acid functional groups. Preferred carboxyvinyl polymers include water-soluble and water-swellable carbomers. Many such carbomers are available under the trade name CARBOPOL® from Lubrizol Corporation. Carbomer polymers are crosslinked, acrylic acid-based polymers. They are cross-linked with allyl sucrose or allylpentaerythritol. Carbomer copolymers are polymers of acrylic acid, modified by $C_{10-30}$ alkyl acrylates, and crosslinked with allylpentaerythritol. A preferred carbomer for use in the compositions of the present invention is a polymer of acrylic acid cross-linked with allyl sucrose or allylpentaerythritol, which is commercially available as CARBOPOL® 974P. The amount of carboxyvinyl polymer present in the suspension compositions of the present invention ranges from about 0.1 to 1.0 w/v %, preferably 0.1 to 0.5 w/v %, and most preferably 0.4 w/v %.

In addition to a carboxyvinyl polymer, the compositions of the present invention utilize a galactomannan-borate system in aqueous solution. A borate anion will condense onto the cis-diol groups of a galactomannan molecule, and may cross-link with a second galactomannan molecule. Cross-linking of borate and galactomannan is influenced by factors such as pH, among others, and such cross-linking in turn influences the viscosity of the solution.

The types of galactomannans that may be used in the present invention are typically derived from guar gum, locust bean gum and tara gum. As used herein, the term "galactomannan" refers to polysaccharides derived from the above natural gums or similar natural or synthetic gums containing mannose or galactose moieties, or both groups, as the main structural components. Preferred galactomannans of the present invention are made up of linear chains of (1-4)-β-D-mannopyranosyl units with α-D-galactopyranosyl units attached by (1-6) linkages.

With the preferred galactomannans, the ratio of D-galactose to D-mannose varies, but generally will be from about 1:2 to 1:4. Galactomannans having a D-galactose:D-mannose ratio of about 1:2 are most preferred. Additionally, other chemically modified variations of the polysaccharides are also included in the "galactomannan" definition. For example, hydroxyethyl, hydroxypropyl and carboxymethylhydroxypropyl substitutions may be made to the galactomannans of the present invention. Non-ionic variations to the galactomannans, such as those containing alkoxy and alkyl (C1-C6) groups are particularly preferred when a soft gel is desired (e.g., hydroxylpropyl substitutions). Substitutions in the non-cis hydroxyl positions are most preferred. An example of non-ionic substitution of a galactomannan of the present invention is hydroxypropyl guar, with a molar substitution of about 0.4. Anionic substitutions may also be made to the galactomannans. Anionic substitution is particularly preferred when strongly responsive gels are desired. A galactomannan is typically present in a formulation of the present invention at a concentration of about 0.01 to about 10 w/v %, preferably at about 0.1 w/v % to about 2.0 w/v %, and most preferably at about 0.1 to about 0.4 w/v %. Preferred galactomannans of the present invention are guar, native guar, and hydroxypropyl guar. In a preferred embodiment of the present invention, native guar is present at a concentration of about 0.2 w/v %. Native guar is particularly preferred, for example, USP or general grade native guar powder obtained from TIC Gums, Inc. A process for producing a particularly preferred native guar is disclosed in co-pending U.S. patent application Ser. No. 12/701,339, entitled "Process for Purifying Guar" filed Feb. 5, 2010.

The borate compounds which may be used in the compositions of the present invention include, but are not limited to, boric acid and other pharmaceutically acceptable salts such as sodium borate (borax) and potassium borate. Borate is typically present at a concentration of 0.2 to 2.0 w/v %, more preferably at a concentration of 0.4 to 0.6 w/v %, and most preferably at about 0.5 w/v %. As used herein, the term "borate" refers to all pharmaceutically suitable forms of borates, including but not limited to boric acid, and alkali metal borates such as sodium borate and potassium borate. Boric acid is the preferred borate used with embodiments of the present invention.

Certain aqueous compositions of the present invention contain a pharmaceutically effective amount of nepafenac or other sparingly soluble particulate compound. As used herein, "sparingly soluble in water" or "sparingly-soluble particulate compound" means a compound or pharmaceutical agent that has a solubility limit in water at 25° C. in the range of 0.001 to 0.1 w/v %. Nepafenac is a known nonsteroidal anti-inflammatory compound, and can be made by known methods. See, for example, U.S. Pat. Nos. 5,475,034 and 4,313,949, the entire contents of which are incorporated by reference. Nepafenac is also known as 2-amino-3-benzoylphenylacetic acid. The topical use of nepafenac and other amide and ester derivatives of 3-benzoylphenylacetic acid to treat ophthalmic inflammation and pain is disclosed in U.S. Pat. No. 5,475,034. The nepafenac compositions of the present invention will generally contain 0.1 to 1.0 w/v %, preferably 0.25 to 0.35 w/v %, and most preferably about 0.3 w/v % nepafenac.

The present inventors have found that decreasing the particle size of nepafenac in certain compositions of the present invention enhances the bioavailability of nepafenac. Preferred compositions accordingly have an average particle size of 50 to to 700 nm, a more preferred average particle size of 100 to 600 nm, and a most preferred average particle size of 400 nm. Methods to produce nanometer and submicron particles of drugs are known, including, but not limited to, milling, high pressure homogenization, or small crystal formation from solutions.

Other sparingly soluble particulate compounds that may be used in embodiments of the present invention include, but are not limited to, nonsteroidal anti-inflammatory compounds, carbonic anhydrase inhibitors, antifungal agents, phosphodiesterase IV inhibitors, receptor tyrosine kinase inhibitors, rho kinase inhibitors, brakykinin agonists, CNP agonists, H1/syk kinase inhibitors, VEGF inhibitors, antibodies and fragments thereof, TNF-α inhibitors, halogenated compounds such as halogenated amino acids, and steroids.

Compositions of the present invention are ophthalmically suitable for application to a subject's eyes. These drops may be delivered from a single dose ampoule which may preferably be sterile and thus render bacteriostatic components of the formulation unnecessary. Alternatively, the drops may be delivered from a multi-dose bottle which may preferably comprise a device which extracts any preservative from the formulation as it is delivered, such devices being known in the art.

The compositions of the present invention may optionally comprise one or more additional excipients and/or one or more additional active ingredients (e.g., pharmaceutical agents). Excipients commonly used in pharmaceutical compositions include, but are not limited to, demulcents, tonicity agents, preservatives, preservative aids, chelating agents, buffering agents, and surfactants. Other excipients comprise solubilizing agents, viscosity-adjusting agents, stabilizing agents, comfort-enhancing agents, polymers, emollients, pH-adjusting agents and/or lubricants.

The compositions of the present invention optionally contain metal chloride salts (such as sodium chloride) or non-ionic tonicity adjusting agents (such as propylene glycol or hydroxyl compounds) as additional tonicity-adjusting agents. Suitable buffering agents include, but are not limited to, phosphates, acetates and the like, and amino alcohols such as 2-amino-2-methyl-1-propanol (AMP). In a preferred composition, a metal chloride such as sodium chloride is present at a concentration of 0.15 to 0.5 w/v %, and most preferably at 0.4 w/v %.

The compositions set forth herein may comprise one or more preservatives. Many ophthalmically acceptable preservatives are known and include, but are not limited to, benzalkonium halides and polyquarternium-1. Most preferred preservatives are benzalkonium chloride ("BAC") and polyquarternium-1. In the case of benzalkonium chloride, the preservative is preferably present in an amount from 0.001 to 0.02%, and most preferably 0.005%.

The compositions of the present invention are preferably isotonic, or slightly hypotonic in order to combat any hypertonicity of tears caused by evaporation and/or disease. This may require a tonicity agent to bring the osmolality of the formulation to a level at or near 250-350 milliosmoles per kilogram (mOsm/kg). The compositions of the present invention generally have an osmolality in the range of 250 to 350 mOsm/kg. The ophthalmic compositions will generally be formulated as sterile aqueous solutions. The term "aqueous" typically denotes an aqueous formulation wherein the formulation is >50%, more preferably >75% and in particular >90% by weight water.

The aqueous compositions of the present invention optionally comprise one or more buffering agents, such as phosphate buffers (e.g., disodium phosphate and monosodium phosphate) and citrate buffers. The buffering agent is chosen based upon the target pH for the composition, which generally ranges from pH 5.0 to 8.5. The target pH for the composition depends upon the chosen ophthalmic drug. In the case of nepafenac, the desired pH is preferably 5.0 to 7.2, and most preferably 6.0. Ophthalmically acceptable pH adjusting agents are known and include, but are not limited to, hydrochloric acid (HCl) and sodium hydroxide (NaOH). In one particularly preferred embodiment the pH of the composition is 5.8 to 6.8.

Nonionic milling agents such as tyloxapol, polysorbate 80, and sodium carboxylmethylcellulose may be included in certain embodiments of the present invention. If present, such milling agents have a concentration of 0.005 to 0.1 w/v % in the compositions of the present invention.

Suitable chelating agents include edetate disodium; edetate trisodium; edetate tetrasodium; and diethyleneamine pentaacetate. Most preferred is edetate disodium. If included, the chelating agent will typically be present in an amount from 0.001 to 0.1 w/v %. In the case of edetate disodium, the chelating agent is preferably present at a concentration of 0.01%.

The compositions of the present invention can be used to treat many ophthalmic disorders. These disorders include, but are not limited to, ocular surface and retinal disorders, glaucoma, dry eye, ocular surface pain, uveitis, scleritis, episcleritis, keratitis, surgically-induced inflammation, endophthalmitis, iritis, atrophic macular degeneration, retinitis pigmentosa, iatrogenic retinopathy, retinal tears and holes, macular edema (e.g., cystoid macular edema), diabetic macular edema, diabetic retinopathy, sickle cell retinopathy, retinal vein and artery occlusion, optic neuropathy, exudative macular degeneration, neovascular glaucoma, corneal neovascularization, cyclitis, sickle cell retinopathy, and pterygium.

In preferred embodiments, a composition of the present invention is administered once a day. The enhanced bioavailability of certain compositions of the present invention allows once-a-day dosing for nepafenac-containing compositions. This dosing regimen improves patient compliance and the odds of successful treatment. However, the compositions may also be formulated for administration at any frequency of administration, including once a week, once every 5 days, once every 3 days, once every 2 days, twice a day, three times a day, four times a day, five times a day, six times a day, eight times a day, every hour, or greater frequency. Such dosing frequency is also maintained for a varying duration of time depending on the therapeutic regimen. The duration of a particular therapeutic regimen may vary from one-time dosing to a regimen that extends for months or years. One of ordinary skill in the art would be familiar with determining a therapeutic regimen for a specific indication.

Certain aspects of the present invention possess numerous advantages. Gelling compositions form clear and colorless gels and do not interfere with vision. The gels are activated by minor pH changes when applied to the eye. Furthermore, guar and carbomer polymers do not have a cloud point when autoclaved, and accordingly provide for easy sterilization. These polymers are also compatible with many commonly used excipients.

The following examples are presented to further illustrate selected embodiments of the present invention.

Example 1

| Ingredient | Amount (w/v %) |
| --- | --- |
| Nepafenac | 0.3 |
| Sodium Carboxymethylcellulose | 0.06 |
| Carbopol 974p | 0.4 |
| Native Guar Gum | 0.2 |
| Boric Acid | 0.5 |
| Sodium Chloride | 0.4 |
| Propylene Glycol | 0.5 |
| Benzalkonium Chloride | 0.005 |
| Disodium EDTA (Edetate Disodium) | 0.01 |
| Sodium Hydroxide/Hydrochloric Acid | q.s. pH 7.0 |
| Purified Water | q.s. 100% |

Example 2

| Ingredient | Amount (w/v %) |
|---|---|
| Rimexolone | 0.01-3.0 |
| Tyloxapol | 0.01-0.1 |
| Carbopol 974 | 0.2-0.6 |
| Guar Gum | 01-0.3 |
| Boric acid | 0.25-1.0 |
| Sodium chloride | 0.2-0.5 |
| Propylene glycol | 0.5-1.5 |
| Disodium EDTA | 0-0.01 |
| Benzalkonium chloride | 0.003-0.01 |
| Hydrochloric acid | q.s. to pH 7.0 |
| Sodium hydroxide | q.s. to pH 7.0 |
| Purified Water | q.s. to 100% |

Example 3

FIG. 1 is a graph showing the concentration of amfenac (a nepafenac metabolite) in the rabbit iris ciliary body (ICB) following a dose of a commercial 0.1 w/v % suspension of nepafenac (NEVANAC®) compared to formulations of 0.3 w/v % nepafenac in carbopol (FID114971) and carbopol/guar/borate (FID114949). The graph demonstrates that the carbopol/guar/borate formulation provides better bioavailability than a similar formulation comprising carbopol only. The NEVANAC formulation had lower amounts of amfenac in the ICB compared to the carbopol/guar/borate formulation.

Example 4

Figure 2A:
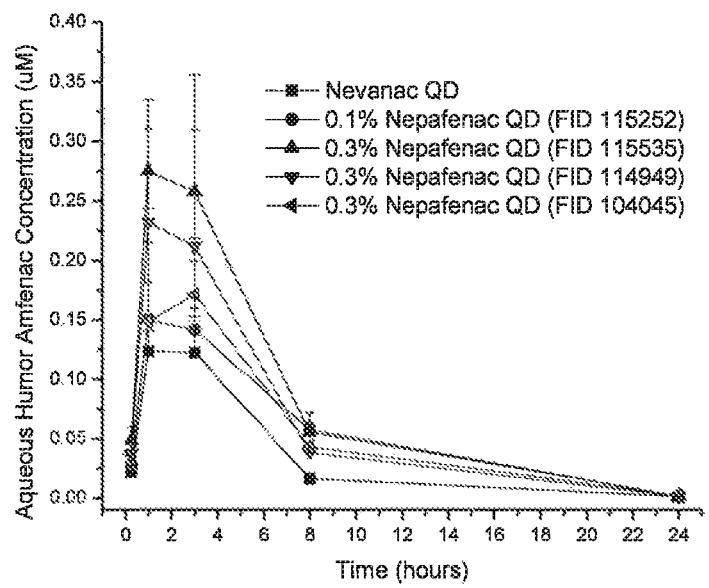
FIGS. 2a and 2b are graphs showing the concentration of amfenac in rabbit aqueous humor and iris ciliary body at various time points following administration of topical nepafenac formulations.
Figure 2B:
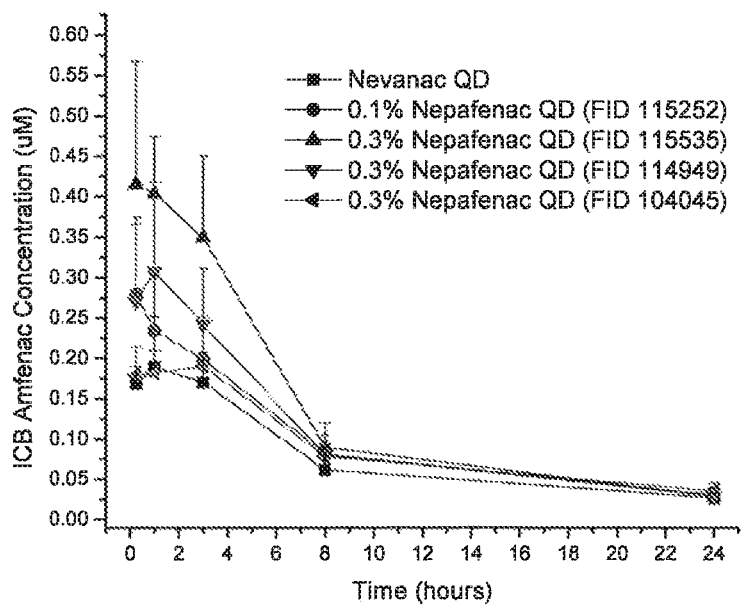

The distribution of nepafenac and its metabolite, amfenac, was studied in New Zealand white rabbits. Rabbits were dosed bilaterally, sacrificed, and aqueous humor (AH) and iris ciliary body (ICB) tissue were analyzed using LC/MS/MS. The data for each time point shown in FIGS. 2a and 2b is the average of concentrations measured from 6 rabbit eyes. Animals dosed TID received three doses 8 hours apart for 4 days, with a single dose in the morning of day 5. Animals dosed QD received one dose for 5 days.

Figure 3A:
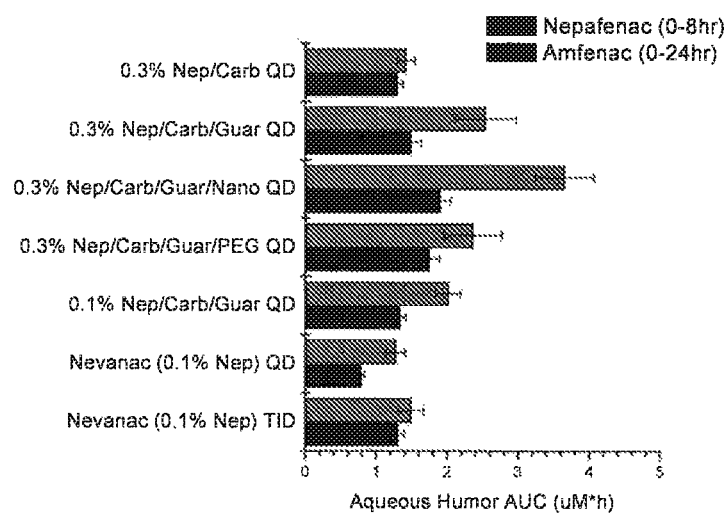
FIGS. 3a and 3b are bar charts showing the area under the curve of concentration vs. time plots of nepafenac and amfenac in rabbit aqueous humor and iris ciliary body after application of topical nepafenac formulations.
Figure 3B:
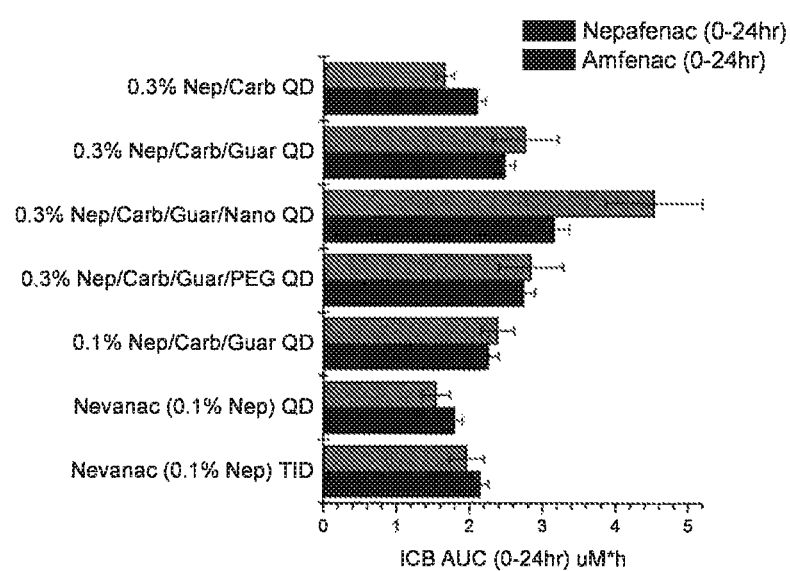

FIGS. 2a and 2b are graphs showing the concentration of amfenac in rabbit aqueous humor and iris ciliary body at various time points following administration of nepafenac formulations. FIGS. 3a and 3b are bar charts showing the area under the curve of concentration vs. time plots of nepafenac and amfenac in rabbit aqueous humor and iris ciliary body after application of topical nepafenac formulations. The figures indicate that the carbopol/guar nepafenac formulations tested consistently produced higher bioavailability than currently marketed nepafenac formulations and formulations having carbopol only. Upon topical ocular administration, the carbopol/guar nepafenac formulation (FID 114949) showed higher bioavailability than the carbopol only formulation (FID 104045). When the nepafenac particle size was reduced to approximately 400 nm, the nanoparticle carbopol/guar formulation (FID 115535) showed increased bioavailability to formulations having larger particle size. All carbopol/guar formulations produced higher aqueous humor and iris ciliary body amfenac concentrations at all time points, as shown in FIGS. 2a and 2b.

The carbopol/guar nanosuspension of nepafenac was made in the following manner. In a 2000 mL glass vessel, was taken 200 g of 2% CARBOPOL® 974P stock solution. To it were sequentially added 5 g boric acid, 4 g sodium chloride and about 200 g of purified water. Stirred well to dissolve and pH was adjusted to 7.0. To this was added 400 g of 0.5% stock solution of guar and mixed thoroughly. To this solution was added 5 g propylene glycol, 5 g of 1% benzalkonium chloride stock solution and 10 g of 1% disodium. EDTA stock solution. The solution pH was checked and adjusted to 950 g by the addition of purified water. This solution was autoclaved at 121° C. for 35 minutes. Upon cooling, 60 g of 5% stock slurry of nepafenac in CMC solution was added. The resulting solution was stirred well and q.s. to 100% of batch size by purified water.

The nepafenac slurry was made in the following manner. In a 1000 mL glass vessel, 10 g sodium carboxymethyl cellulose (CMC) 7LF PH was allowed to hydrate for 2 hours, and then autoclaved for 35 minutes at 121° C. A 3-5% slurry of nepafenac was aseptically prepared in the above CMC solution. The suspension was homogenized using a hand held homogenizer for 10 min. at 5000-10000 RPM. The slurry was then aseptically milled with a Netszch Minicer High Energy Mill (HEM) using 140 mL of 0.2 mm Zr beads in a clean room for 30 min at 3000 RPM to achieve the targeted particle size. The resulting slurry was checked for particle size.

The present invention and its embodiments have been described in detail. However, the scope of the present invention is not intended to be limited to the particular embodiments of any process, manufacture, composition of matter, compounds, means, methods, and/or steps described in the specification. Various modifications, substitutions, and variations can be made to the disclosed material without departing from the spirit and/or essential characteristics of the present invention. Thus, the following claims are intended to encompass within their scope modifications, substitutions, and variations to processes, manufactures, compositions of matter, compounds, means, methods, and/or steps disclosed herein. All patents and publications mentioned in the specification are herein incorporated by reference to the same extent as if each individual publication was specifically and individually indicated to be incorporated by reference.

What is claimed is:

1. A topically administrable aqueous ophthalmic suspension composition comprising:
   carbomer at a concentration of 0.1 to 0.5 w/v %;
   guar at a concentration of 0.1 to 0.4 w/v %;
   borate at a concentration of 0.4 to 2.0 w/v %; and
   a sparingly soluble particulate compound, said compound having a solubility in water at 25° C. of 0.001 to 0.1 w/v % and a particle size of 50 to 700 nm, and wherein said sparingly soluble particular compound is nepafenac at a concentration of 0.25 to 0.35 w/v %.

2. A composition according to claim 1, further comprising a pH-adjusting agent in an amount sufficient to cause the composition to have a pH of 5.0 to 7.2.

3. A composition according to claim 1, further comprising a tonicity-adjusting agent in an amount sufficient to cause the composition to have an osmolality of 250 to 350 mOsm/kg.

4. A composition according to claim 1 wherein said carbomer is at a concentration of 0.4 w/v %.

5. A composition according to claim 1 further comprising a milling agent at a concentration of 0.005 to 0.1 w/v %.

6. A composition according to claim 5 wherein said milling agent is a surfactant or polymer.

7. A composition according to claim 6 wherein said milling agent is sodium carboxylmethylcellulose.

8. A composition according to claim 1 further comprising a metal chloride salt tonicity-adjusting agent.

9. A composition according to claim 8 wherein said metal chloride salt is sodium chloride at a concentration of 0.4 w/v %.

10. A composition according to claim 1 further comprising a non-ionic hydroxyl compound as a tonicity-adjusting agent.

11. A composition according to claim 1 further comprising both a preservative and a chelating agent.

12. A composition according to claim 11 wherein the preservative is benzalkonium chloride at a concentration of 0.005 w/v % and the chelating agent is edetate disodium at a concentration of 0.01 w/v %.

13. A composition according to claim 1 comprising 0.4 w/v % carbomer, 0.2 w/v % guar, 0.5 w/v % boric acid, and 0.3 w/v % nepafenac.

14. A composition according to claim 13 wherein said nepafenac has an average particle size of 400 nm.

15. A topically administrable ophthalmic suspension composition consisting essentially of
   a) 0.3 w/v % nepafenac having a particle size of 50 to 700 nm;
   b) 0.4 w/v % carbomer;
   c) 0.2 w/v % guar;
   d) 0.5 w/v % boric acid;
   e) 0.06 w/v % sodium carboxymethylcellulose;
   f) 0.4 w/v % sodium chloride;
   g) 0.5 w/v % propylene glycol;
   h) a pH-adjusting agent in an amount sufficient to cause the composition to have a pH of 7.0;
   i) 0.005% (w/v) benzalkonium chloride;
   j) 0.01% edetate disodium; and
   k) purified water.

\* \* \* \* \*